US00PP08278P

United States Patent [19]

Dorieux

[11] Patent Number: Plant 8,278

[45] Date of Patent: Jun. 29, 1993

[54] HYBIRD TEA ROSE PLANT NAMED DOR JURE

[75] Inventor: Francois Dorieux, Montagny Loire, France

[73] Assignee: Roses by Fred Edmunds, Inc., Wilsonville, Oreg.

[21] Appl. No.: 816,877

[22] Filed: Jan. 2, 1992

[51] Int. Cl.[5] ..... A01H 5/00

[52] U.S. Cl. ..... Plt./12

[58] Field of Search ..... Plt./11, 12

*Primary Examiner*—Howard J. Locker

*Attorney, Agent, or Firm*—Christie, Parker & Hale

[57] ABSTRACT

A new variety of hybrid tea rose having red and silver flowers.

1 Drawing Sheet

SUMMARY OF THE INVENTION

The present invention relates to a new and distinct variety of rose plant of the hybrid tea rose class, which was originated by my crossing as seed parent the variety known as 'Pharaon' and as pollen parent the variety known as 'Osiria'. The varietal denomination of this new rose is 'Dor Jure'.

Among the novel characteristics possessed by this new variety which distinguishes it from its parents and all other varieties of which I am aware are its attractive bicolor flowers having red coloring on the petals top surface and silver coloring on the petals's reverse (undersurface). The flowers are large and are borne singly in a manner typical of hybrid tea varieties and on a plant suitable for growing outdoors in gardens.

Asexual reproduction by propagation by budding of the new variety as performed in Clackamas County, Oreg. shows that the foregoing and other distinguishing characteristics come true to form and are established and transmitted through succeeding propagations. The new variety can be asexually propagated by budding, grafting, micropropagation and from cuttings.

BRIEF DESCRIPTION OF ILLUSTRATION

The accompanying illustration shows typical specimens of the flowers and vegetative growth of the new variety depicted in color as nearly true as it is reasonably possible to make the same in a color illustration of this character. Colors may vary depending upon growing conditions under different climate, soil, and cultivation conditions.

DETAILED DESCRIPTION OF THE NEW VARIETY

The following is a detailed description of my new variety, with color terminology in accordance with The Royal Horticultural Society Colour Chart (R.H.S.C.C.). The terminology used in the color descriptions herein refers to plate numbers in the aforementioned color chart.

Parentage: Seedling.

*Seed parent.*—'Pharaon'.

*Pollen parent.*—'Osiria'.

Class: Hybrid tea.

The following further horticultural observations were made of specimens gorwn outdoors in Clackamas County, Oreg. in the month of September.

FLOWER

Blooming habit: Continuous.

A. Bud:

(1) *Size.*—Large.

(2) *Form.*—Ovoid.

(3) *Color.*—When sepals first divide, near 45A to 52A-B; when petals begin to unfurl, near 45B.

(4) *Sepals.*—Longer than bud, very fancy.

*Peduncle.* Length — medium. Aspect — straight. Strength — erect. Color — near 144B.

B. Bloom:

(1) *Size.*—Average size when fully expanded — about 5 inches.

(2) *Borne.*—Singly, one to a stem.

3) *Form.*—Spiral, imbricated, at first petals loosely roll outward, opens flat.

(4) *Petalage.*—Number of petals under normal conditions — about 40.

(5) *Color.*—After sepals fall and petals unfurl, outer petals (top surface) and at flower center, near 45A to near 51A, 52A. Innter petals (top surface) where petals bunch have deep color tones; petals lighten upon aging, approaching near 52B-D. Petal reverse surface exhibits nominal "silver" color, near 55D with some near 36C, D coloration at times. Petal color near point of petal attached is near 5C. General tonality from a distance is attractive red and "silver" bicoloration. As blooms age, red coloring lightens.

c. Petals:

(1) *Texture.*—Thick.

(2) *Appearance.*—Inside velvety, outside satiny.

(3) *Form.*—Oval, deltoid, wider than long.

(4) *Arrangement.*—Spiral imbrication.

(5) *Petaloids in center.*—Few.

(6) *Persistence.*—Drop off cleanly.

(7) *Fragrance.*—Slight, spicy.

(8) *Lasting Quality.*—Very long lasting on plant and after cutting.

REPRODUCTIVE ORGANS

A. Stamens, filaments and anthers:

*Arrangement and color.*—Regularly arranged around styles, numerous, short.

*Color.*—Filaments near 23A, anthers near 11B.

B. Pollen:
*Color.*—Near 11A.
C. Styles: Uneven lengths. long, thin.
D. Stigmas: Near 18A.
E. Hips: Not observed.

PLANT

A. Form: Upright.
B. Growth: Very vigorous, free branching.
*Height attained.*—About 6 feet in September.
C. Foliage: Usually compound 3 and 5 leaflets.
(1) *Size.*—Large.
(2) *quantity.*—Abundant.
(3) *Color.*—New foliage: Upper side — near 147A. Underside — near 147C. Old foliage: Upper side — near 139A. Underside — near 139B.
(4) *Shape.*—Obovate, acute.
(5) *Texture.*—Upper side is glossy, leathery; Underside is matte.
(6) *Edge.*—Serrate.
(7) *Serration.*—Simple, light.
(8) *Leaf stem.*—Color — near 147A; underside near 138B.

(9) *Stipules.*—Long, over half way to first leaflets, slightly bearded.
(10) *Resistance to disease.*—Blackspot—excellent. Mildew—excellent. Rust—excellent.
D. Wood:
(1) *New wood.*—Color — near 139C. Bark — smooth.
(2) *Old wood.*—Color — near 144A. Bark — smooth.
E. Thorns:
*Quantity (main stalk).*—many, scattered, small.
*On laterals from stalk.*—Many, scattered.
*Form.*—Slightly recurved.
*Length.*—Medium.
*Color.*—Near 154A (young) to near 144B (old).
*Position.*—Irregular.
*Prickles.*—Many, profuse.
F. Winter hardiness: Winter hardy with some protection needed in severe climates.

I claim:

1. A new and distinct variety of rose plant of the hybrid tea rose class, substantially as shown and descirbed.

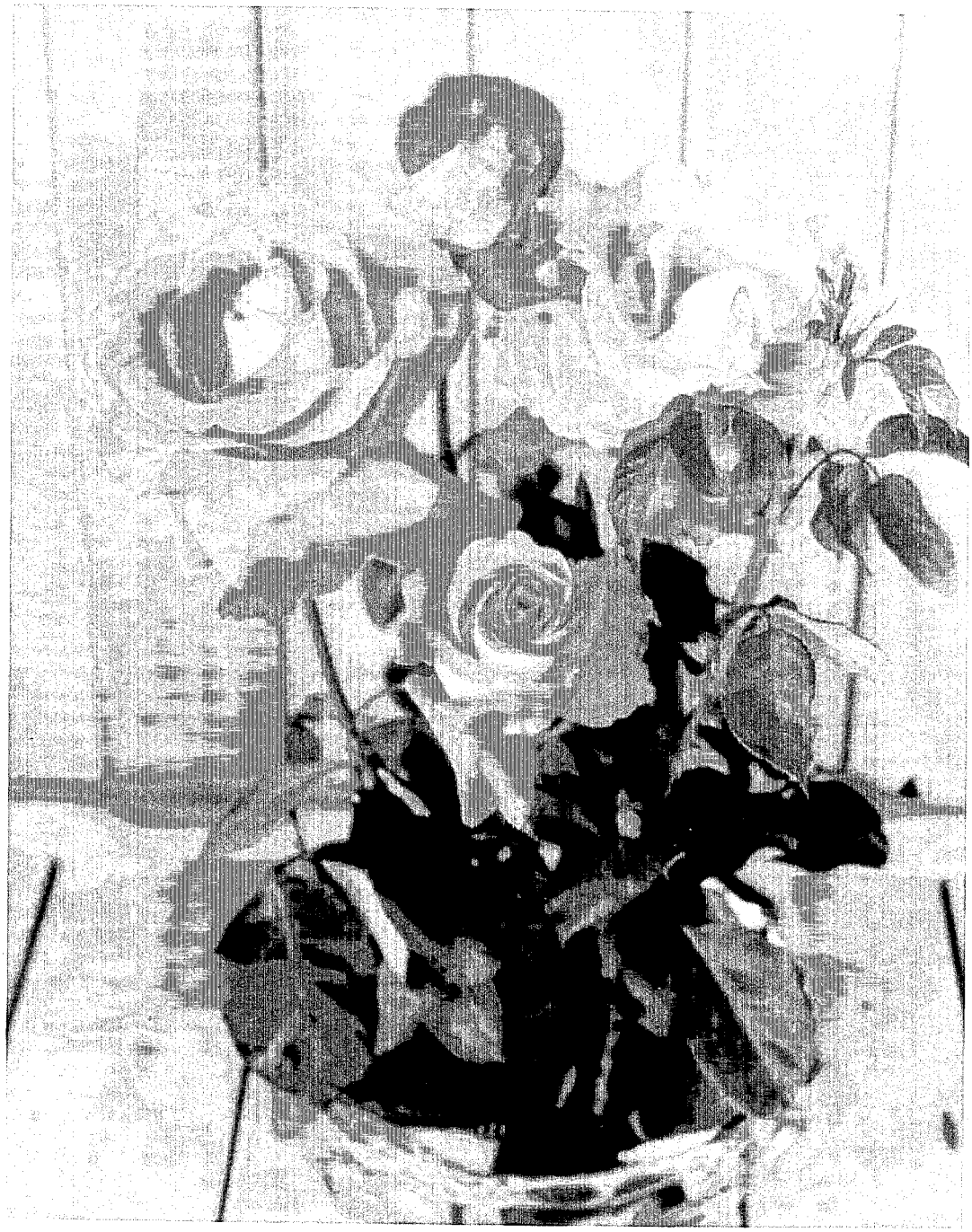

* * * * *